United States Patent [19]

Missirlian et al.

[11] Patent Number: 5,019,035

[45] Date of Patent: May 28, 1991

[54] CUTTING ASSEMBLY FOR SURGICAL CUTTING INSTRUMENT

[75] Inventors: Berge Missirlian, Pasadena; Tamer Akkas, Mission Viejo; Wayne A. Cook, Igo, all of Calif.

[73] Assignee: Alcon Surgical, Inc., Fort Worth, Tex.

[21] Appl. No.: 362,806

[22] Filed: Jun. 7, 1989

[51] Int. Cl.$^5$ ............................................. A61B 17/32
[52] U.S. Cl. ...................................... 604/22; 606/171
[58] Field of Search ....................... 606/107, 171, 170; 604/22

[56] References Cited

U.S. PATENT DOCUMENTS

| | | |
|---|---|---|
| 3,776,238 | 12/1973 | Peyman et al. |
| 3,815,604 | 6/1974 | O'Malley et al. |
| 3,884,238 | 5/1975 | O'Malley et al. |
| 3,994,297 | 11/1976 | Kopf . |
| 4,011,869 | 3/1977 | Seiler, Jr. |
| 4,099,529 | 7/1978 | Peyman . |
| 4,111,207 | 9/1978 | Seiler, Jr. |
| 4,200,106 | 4/1980 | Douvas et al. |
| 4,210,146 | 7/1980 | Banko . |
| 4,246,902 | 1/1981 | Martinez . |
| 4,314,560 | 2/1982 | Helfgott . |
| 4,316,465 | 2/1982 | Dotson, Jr. |
| 4,428,748 | 1/1984 | Peyman et al. |
| 4,449,550 | 5/1984 | Ranalli . |
| 4,530,356 | 7/1985 | Helfgott et al. |
| 4,530,359 | 7/1985 | Helfgott et al. |
| 4,570,632 | 2/1986 | Woods . |
| 4,577,629 | 3/1986 | Martinez . |
| 4,601,290 | 7/1986 | Effron et al. |
| 4,655,743 | 4/1987 | Hyde . |
| 4,674,502 | 6/1987 | Imonti . |
| 4,678,459 | 7/1987 | Onik et al. |
| 4,696,298 | 9/1987 | Higgins et al. |

OTHER PUBLICATIONS

"MicroVit Vitrectomy System", Copyright 1983.
International Publication No.: WO 81/01363, "Coaxial Tube Surgical Suction Cutter Tip", 1981.

*Primary Examiner*—Michael H. Thaler
*Attorney, Agent, or Firm*—Lowe, Price, LeBlanc, Becker & Shur

[57] ABSTRACT

A microsurgical cutting instrument is disclosed which is provided with a cutting probe assembly wherein the inner and outer cutting members thereof are swaged and the inner cutting member is bent towards the outer cutting member, so as to maintain a preselected relationship of the cutting edges.

18 Claims, 4 Drawing Sheets

CUTTING ASSEMBLY FOR SURGICAL CUTTING INSTRUMENT

BACKGROUND OF THE INVENTION

The present invention relates generally to surgical cutting instruments and, more particularly, to microsurgical cutting instruments and an improved cutting probe assembly therefor.

In microsurgery, particularly ophthalmic surgery, smooth cutting action of the vitreous tissue is highly desirable. Many types of surgical cutting instruments for aiding ophthalmic physicians have been proposed. In general, microsurgical instruments of this kind include a cutting probe assembly insertable into the patient. The cutting probe assembly can be inserted into the eye, through an incision in the cornea or sclera. Included in such a probe assembly are generally coaxially extending inner and outer cutting members. A port or opening extends radially through the outer cutting member adjacent a distal end thereof and through which tissue is aspirated for subsequent cutting and continued aspiration. Disposed for movement within the outer cutting member is the inner cutting member which cooperates with the former for effecting the cutting action.

It has been determined that when the motion of the inner cutting member is rotational relative to the outer cutting member, the vitreous and other tissue have an undesirable tendency of being pulled while being cut. Current practice prefers providing a reciprocating longitudinally moving inner cutting member that moves relative to a cutting port of the outer cutting member. This provides a cleaner chopping or guillotine type of action to the tissue drawn through the port. Many drive systems are available for reciprocating the inner cutting member, such as disclosed in U.S. Pat. Nos. 4,246,902 and 4,674,502. Many of the known microsurgical cutting instruments of the latter type have the inner and outer cutting members reciprocate along a common axis with sufficient radial clearance therebetween (e.g. a few thousandths of an inch) to effect the desired cutting or shearing action on the tissue. For successful cutting it, is important to have a predetermined cutting clearance between the reciprocating coaxial members. However, this is often difficult to achieve on a consistent basis. In U.S., Pat. No. 4,210,146 there is disclosed a surgical instrument having a bendable spring-type inner cutting blade which changes in shape as it reciprocates along a path and engages a tapered configuration of an inner wall of the outer member. Another known approach described generally in U.S. Pat. No. 4,696,298 is to flare the end of the inner cutting member into an elliptical shape so as to achieve a spring-tension in order to hold the cutting blade into conformity with the inner diameter of the outer member.

From the foregoing, it is clear that there is a continuing effort to improve the cutting efficiency of microsurgical cutting instruments by attempting to provide a constant and clean shearing cut in an inexpensive and reliable manner.

SUMMARY OF THE INVENTION

It is an object of the present invention to provide an improved surgical instrument, especially of the microsurgical type. According to this invention, there is provided a surgical cutting instrument comprising a handpiece assembly and a cutting probe assembly attached thereto. The cutting probe assembly comprises inner and outer tubular cutting members. The outer cutting member is formed with a port or opening adjacent a distal end thereof and has at least a cutting edge. Disposed for movement within the outer tubular cutting member is the inner cutting member and also has a cutting edge. The cutting edges are dimensioned and oriented so as to provide a cutting or shearing action on body tissue that is drawn through the port. The cutting probe assembly is communicable with a source of vacuum so as to facilitate aspiration of cut body tissue and body fluids through the cutting probe assembly. The inner cutting member has a distal end portion which is bent at a predetermined angle relative to a longitudinal axis thereof, so that a distal tip having the cutting edge terminates adjacent the port of the outer cutting member. Accordingly, during relative reciprocation, a clean cutting or shearing action of body tissue drawn through the port is effected.

The present invention also contemplates an improved cutting probe assembly for use in connection with surgical instruments of the type wherein components thereof are reciprocated for obtaining a cutting action.

Among the other objects and features of the present invention are the provisions of an improved surgical cutting instrument for cleanly and effectively cutting body tissue; the provision of an improved cutting probe assembly of such a surgical instrument which resiliently maintains proper orientation and spacing of an inner cutting member relative to an outer cutting member during relative reciprocating movement; and, the provision of a cutting probe assembly of the above type which is a simple and inexpensive in construction.

Still other objects and further scope of applicability of the present invention will become apparent from the detailed description to follow when taken in conjunction with the accompanying drawings in which like parts are designated the like reference numerals throughout several views.

DETAILED DESCRIPTION

Figure 1:
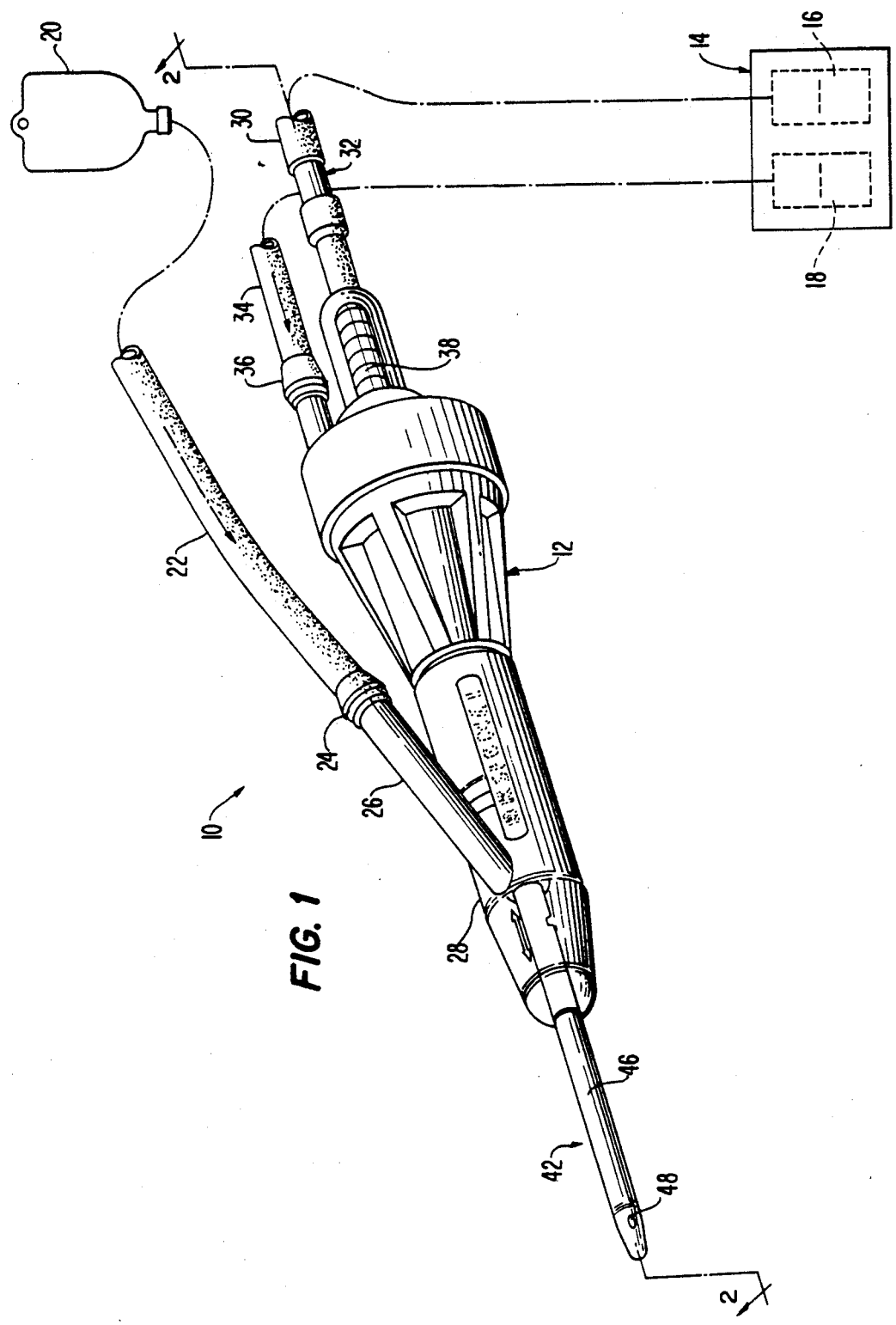
FIG. 1 is a perspective view of a surgical cutting instrument of the present invention.

Referring to the drawings there is illustrated a microsurgical cutting instrument being generally designated by reference numeral 10. This instrument 10 is of the type described in commonly owned and copending patent application Ser. No. 07/116,796 filed on Nov. 11, 1987 now Pat. No. 4,909,249. Only details of the construction and operation of the cutting instrument 10 believed necessary to understand the present invention will be presented herein.

The cutting instrument 10 shown in FIGS. 1-3 includes a vitrectomy handpiece assembly 12 connected to a low pressure pump system 14 which provides a suitable vacuum source 16 and a pressure source 18 for purposes which will be made apparent. A source of irrigation fluid, such as a bottle 20, is to be located at a predetermined height above the surgical site. The irrigation bottle 20 is connected by silicone or PVC irrigation tubing 22 to an infusion fitting 24 on an infusion sleeve 26 of an infusion cap 28. A silicone tubing aspirator or vacuum line 30 fluidically couples the vacuum source 16 to a vacuum fitting 32 on the handpiece assembly 12. A silicone pressure line 34 fluidically couples the pressure source 18 to a pressure line fitting 36. Both the vacuum fitting 32 and the pressure line fitting 36 are formed at separate locations relative to each other on an end cap 38 of the handpiece assembly 12.

Figure 2:
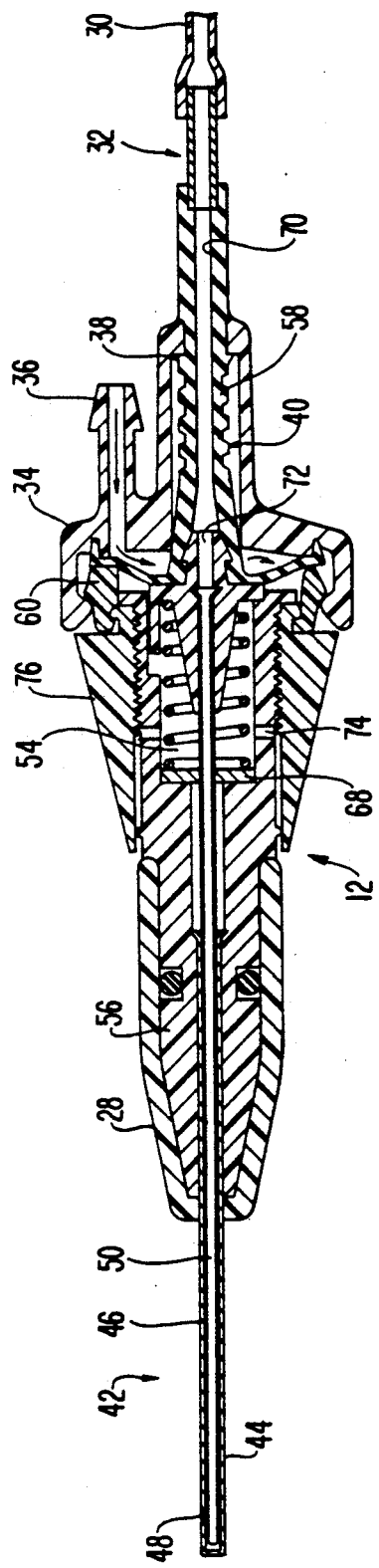
FIG. 2 is a cross-sectional view of the surgical cutting instrument of FIG. 1 in one condition of operation.
Figure 4:
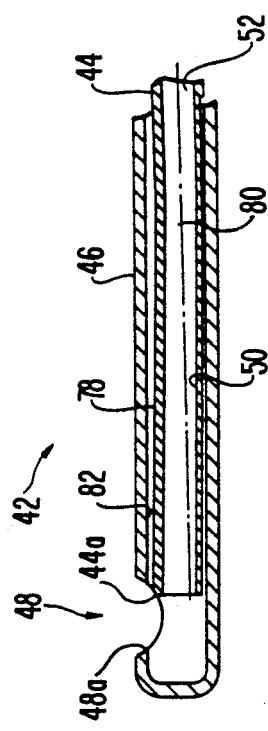
FIG. 4 is an enlarged and fragmented cross-sectional view illustrating the orientation of components forming the cutting probe assembly of the cutting instrument.
Figure 3:
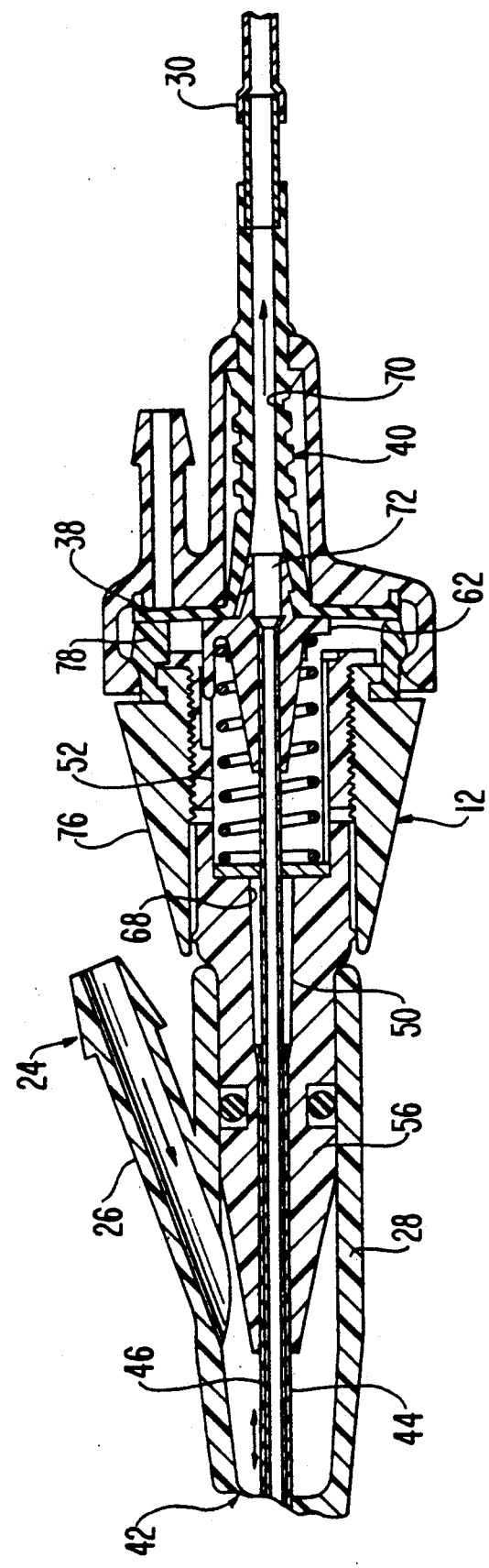
FIG. 3 is a fragmented view similar to FIG. 2 but with the instrument in another condition of operation.

The handpiece assembly 12 houses a diaphragm assembly 40 (FIGS. 2 & 3). The diaphragm assembly 40 is operatively secured to a cutting probe assembly 42 as will be discussed. Included in the cutting probe assembly 42 is an inner tubular cutting member 44 which is adapted to rapidly reciprocate within a stationary outer tubular cutting member 46. The outer cutting member 46 has a cutting orifice or port 48 (FIGS. 1, 2, and 4) located adjacent the forward or distal tip thereof which defines a cutting edge 48a. In this embodiment the distal tip has a closed and leakfree end. The inner cutting member 44 is formed with a cutting edge 44a (FIG. 4), at its distal end or tip. When the cutting edge 44a moves reciprocally relative to the cutting edge 48a, a cutting or shearing action is effected. The inner cutting member 44 defines an axially extending passageway 50 which allows the vacuum source 16 to draw or aspirate vitreous tissue and other matter in through the port 48 so as to be chopped in a guillotine fashion.

Figure 5:
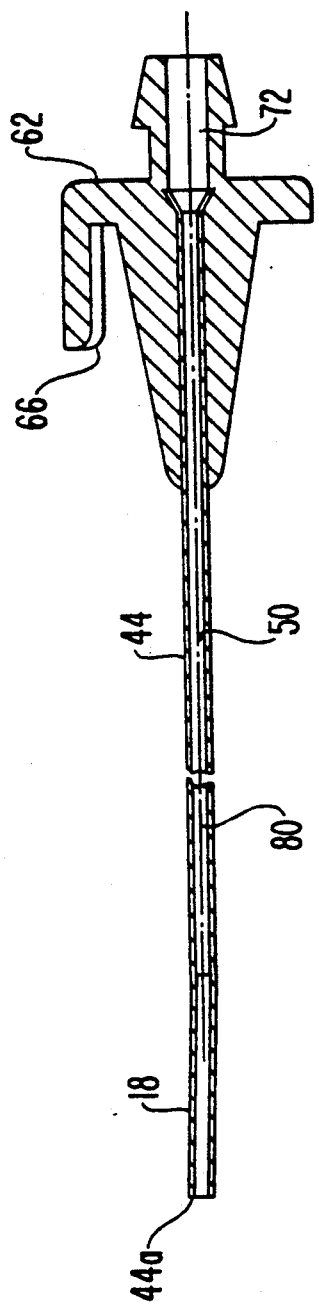
FIG. 5 is a cross-sectional view of an inner cutting member of the surgical cutting instrument; and, FIG. 6 is an end view of the tip of the inner cutting member.
Figure 6:
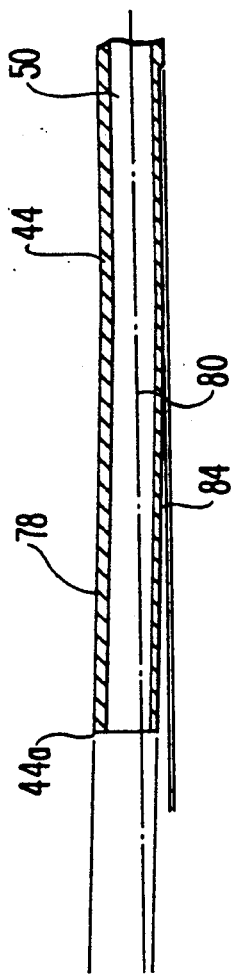
Figure 7:
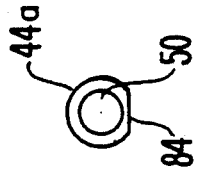
FIG. 7 is a cross-sectional view of the tip of the inner cutting member.

The diaphragm assembly 40 serves for reciprocating the inner cutting member 44 relative to the stationary outer cutting member 46 for achieving the desired cutting action. In this regard, pulsating pressurized air from the pressure source 18 flows through the pressure line 34 against the bias of the diaphragm assembly 40. This drives the inner cutting member 44 forwardly (FIG. 2). For returning the inner cutting member 44 to its retracted position (FIG. 3), there is provided a compressible biasing-spring 52 which is disposed within a chamber 54 of the diaphragm assembly 40 and also by the vacuum affect thereon by the vacuum source 16. The diaphragm assembly 40 is formed of a suitable resilient material, such as medical grade silicone and includes an expandable and contractible bellows portion 58, an integral diaphragm flange 60 and a separate diaphragm hub member 62 (FIGS. 2, 3 and 5). The diaphragm hub 62 is slidable within an elongated body member 56. The inner cutting member 44 is secured to the hub 62 as by an outwardly-flaring tube flange. The outer cutting member 46 is fixedly attached to the body member 56 by an outwardly flaring tube flange. The diaphragm hub 62 is formed with a seat 66 into which is seated the bias spring 52. The forward end of the spring 52 is positioned against a gasket member 68, the latter of which is sandwiched between a hole in the body member 56 and the spring 52. A diaphragm passageway 70 extends longitudinally along the diaphragm assembly 40 and is coextensive with a hub passageway 72 of the diaphragm hub 62. Both of the passageways 70 and 72 communicate with the axial passageway 50 of the inner cutting member 44 and with the vacuum line 30.

When the pressure in the pressure line 34 is not at its peak, the inner cutting member 44 is positioned in its rearward position, at best illustrated in FIG. 3. In this position the port 48 is open (FIG. 4) so that vitreous material can be aspirated therethrough. When the pressure in the pressure line 34 is increased, the pressurized air causes the diaphragm assembly 40 to expand and the diaphragm hub 62 to be pushed forwardly against the bias of the spring 52. The inner cutting member 44 is thereby caused to move forward so that its cutting edge 44a passes the cutting edge 48a and shears or cuts the drawn-in vitreous material. In this embodiment, the cutting edges will slidably engage. In other contemplated embodiments, the edges can have a slight clearance therebetween, so that, preferably, the clearance does not exceed 0.00015 inch.

As the diaphragm assembly 40 moves forward, the air in the chamber 54 is expelled through relief holes 74 formed in the body member 56. Alternatively air is drawn in through the holes 74 when the diaphragm assembly 40 moves backward. The relief holes 74 are positioned so that they cannot be closed off by the user's fingers or other means.

Adjustments to the size of the port 48 can be made by positioning the adjustment nut 76 as is described in the aforenoted copending application. Briefly described however, as the adjustment nut 76 is turned, the adapter 78, the end cap 38 and the diaphragm hub 62 are all moved forwardly or backwardly depending on the direction in which the adjustment nut 76 is turned. As the diaphragm hub 62 is moved relative to the body member 56, the normal longitudinal position of the inner cutting member 44 relative to the outer cutting member 46 is also adjusted.

Reference is now made back to the cutting probe assembly 42 which is constructed so as to constantly maintain a precise orientation of the cutting edges 44a, 48a of the respective inner and outer cutting members 44 and 46. The cutting probe assembly 42 provides for efficient and clean cutting action while substantially minimizing or avoiding pulling or tearing on the drawn-in vitreous material. Towards the foregoing ends, the inner cutting member 44 has a distal end portion 78 which is bent at a critical angle relative to its longitudinal axis 80 so that the cutting edge 44a is preferably engaged with respect to the inner walls 82 adjacent the cutting edge 48a of the outer cutting member 46, but can also be slightly spaced therefrom. The inclined distal end portion 78 is provided with a resilient or spring-like property which facilitates maintaining the cutting edge 44a in a proper cutting orientation relative to the cutting edge 48a. In a preferred embodiment, the distal end portion 78 is disposed at an acute angle of about 1¼° relative to the longitudinal axis 80 (FIG. 4) with a tolerance of plus or minus ¼°. In this embodiment, the length of the inclined distal end portion 78 is approximately 0.195 inches long. The distal end portion 78 has a flattened relief segment 84 to eliminate possible interference thereof with the inner walls 82. The relief segment 84 is disposed on the surface of the inner cutting member 44 which is remote from the port 48. The axial extent of relief segment 84 is about 0.250 inch and extends beyond the junction of the distal end portion 78 and the elongated remainder of the inner cutting member 44. The distal end portion has a bend radius of about 0.06 inch. The relief segment 84 has a relief of about 0.0020 inch plus 0.0010 inch and minus 0.0005 inch.

Reference is now made back to the cutting port 48. In the present embodiment, the port 48 is generally circular in configuration and has a radius which is, preferably, substantially identical to the outer radius of the outer cutting member 46. It has been found that this geometrical relationship enhances cutting performance. In this embodiment, the depth of the port 48 can be in a range of about 0.011 inch to 0.012 inch.

For forming the side port 48a a suitable technique, such as electro-chemical grinding is used.

Both inner and outer cutting members 44, 46, respectively can be made of tungsten carbide or other suitable material, such as any suitable hypodermic grade metal. The outer cutting tube member 46 can be welded and a mandrel is used for controlling its ultimate shape.

The cutting probe assembly 42 contemplates that both the inner and outer cutting tube members 44 and 46 be swaged at least adjacent the tips thereof. This is to effectively control the inner and outer diameters thereof. In one embodiment, the outer diameter of the inner cutting member 44 is about 0.0250 inch and the inner diameter of the outer cutting member 46 is about 0.0251 inch. It has been found that swaging of the tips of both the inner and outer cutting members 44 and 46 allows the gap or radial clearance therebetween to be better controlled. For example in this embodiment, it is preferable to avoid having the clearance between the inner diameter of the outer cutting member 46 and the outer diameter of the inner cutting tube member 44 exceed 0.00015 inch. It has also been found that by swaging the inner walls 82 adjacent the port 42 to a mirror-like finish, such enhances the cutting action.

It is believed from the foregoing detailed description of the construction of the microsurgical instrument that its operation is understood. Although the primary use of the subject surgical cutting instrument is for ophthalmic surgery, such as vitrectomy, other surgical uses on or in other parts of the body are possible. Moreover, the cutting probe assembly as contemplated by this invention can be used with other microsurgical instruments of the type which effect cutting by rapid reciprocation.

Since certain changes maybe made in the above described instrument and cutting probe assembly without departing from the scope of the invention herein involved it is intended that all matter contained in the description or shown in the accompanying drawings shall be interpreted as illustrative and not in a limiting sense.

What is claimed is:

1. A surgical cutting instrument comprising: a handpiece assembly;
   a cutting probe assembly allowing aspiration of body tissue therethrough and being attached to said handpiece assembly and including outer and inner cutting assemblies;
   said outer assembly including an outer tubular cutting member having a distal end portion defining a cutting port through which body tissue is aspirated, and a cutting edge;
   said inner cutting assembly including an inner tubular cutting member disposed inside of and continuously spaced along its entire length from said outer tubular cutting member;
   reciprocating means coupled to said handpiece assembly for rapidly reciprocating said inner cutting member axially within and relative to said outer cutting member;
   said inner cutting member having a distal end portion with a cutting edge formed thereon, said end portion of said inner member is angularly inclined relative to a longitudinal axis of said inner cutting member and is sized, shaped and inclined so as to have a preselected relationship with said cutting edge of said outer cutting member, said cutting edge of said inner member being resiliently maintained in the preselected relationship to cooperate with said cutting edge of said outer member to effect cutting of tissue aspirated through said port as said inner and outer cutting members are reciprocated with respect to each other;
   said port has a radius which is generally equal to an outer radius of said outer cutting member so as to improve the cutting edge;
   the predetermined relationship between said inner and outer cutting members defines a clearance therebetween; and
   said inner cutting member has a relief surface formed which extends along the entire length of said distal end portion from a junction of said end portion and an adjacent portion of said inner cutting member, said relief surface being on a surface remote from said port.

2. The instrument of claim 1 wherein, said distal end portion of said inner cutting member is disposed at an angle of about one and a half degrees plus or minus one-quarter degree relative to a longitudinal axis of said inner cutting member.

3. The instrument of claim 1 wherein at least distal end portions of said inner and outer cutting members are swaged.

4. The instrument of claim 3 wherein the inner surface of said outer cutting member adjacent said port is swaged to a mirror-like finish so as to improve cutting action.

5. The instrument of claim 4 wherein said distal end portion of said inner cutting member is opened and said distal end portion of said outer cutting member is closed.

6. The instrument of claim 1 wherein said clearance is no greater than 0.00015 inch.

7. The instrument of claim 1 wherein, said relief surface has a relief thereof about 0.0020 inch.

8. The instrument of claim 7 including,
   said relief surface being 0.250 inch long.

9. The instrument of claim 1 wherein
   said distal end portion of said inner cutting member is about 0.195 inch long.

10. The assembly of claim 9 including,
    said distal end portion of said inner cutting member is disposed at an angle of about one and a half degrees plus or minus one-quarter degree relative to a longitudinal axis of said inner cutting member.

11. The assembly of claim 10 wherein the inner surface of said outer cutting member adjacent said port is swaged to a mirror-like finish so as to improve cutting action.

12. The assembly of claim 11 wherein said distal end portion of said inner cutting member is opened and said distal end portion of said outer cutting member is closed.

13. The assembly of claim 9 wherein at least distal portions of said inner and outer cutting members are swaged.

14. A cutting probe assembly for use with a surgical cutting instrument of the type having a handpiece assembly, the handpiece assembly including means for effecting reciprocation of said probe assembly; said cutting probe assembly allowing aspiration of body tissue therethrough and being adapted to be attached to said handpiece assembly; said probe assembly comprising outer and inner cutting assemblies;

said outer cutting assembly including an outer tubular cutting member fixedly attached at a proximal end to said handpiece assembly and having a distal end portion defining a cutting port through which body tissue is aspirated, said outer tubular member having a cutting edge;

said inner cutting assembly including an inner tubular cutting member disposed inside of and continuously spaced along its entire length from said outer tubular cutting member;

said inner cutting member connected to the reciprocating means for reciprocating movement relative to and within said outer cutting member;

said inner cutting member having a distal end portion with a cutting edge formed thereon, said end portion of said inner member is angularly inclined relative to a longitudinal axis of said inner cutting member and is sized, shaped and inclined so as to maintain a preselected relationship with said cutting edge of said outer cutting member, said cutting edge of said inner member being resiliently maintained in the preselected relationship to cooperate with said cutting edge of said outer member to effect cutting of tissue aspirated through said port as said inner and outer cutting members are reciprocated with respect to each other;

said port has a radius which is generally equal to an outer radius of said outer cutting member so as to improve the cutting action;

the preselected relationship between said inner and outer cutting members defines a clearance therebetween; and said inner cutting member has a relief surface formed which extends along the entire length of said distal end portion from a junction of said end portion and an adjacent portion of said inner cutting member, said relief surface being on a surface remote from said port.

15. The assembly of claim 14 wherein said clearance is no greater than 0.00015 inch.

16. The assembly of claim 14 wherein, said relief surface has a relief thereof about 0.0020 inch.

17. The assembly of claim 16 including,
said relief surface being 0.250 inch long.

18. The assembly of claim 14 wherein
said distal end portion of said inner cutting member is about 0.195 inch long.

* * * * *